(12) United States Patent
Schweinfurth et al.

(10) Patent No.: US 11,094,124 B1
(45) Date of Patent: Aug. 17, 2021

(54) AUGMENTED REALITY PHARMACEUTICAL INTERFACE

(71) Applicant: WALGREEN CO., Deerfield, IL (US)

(72) Inventors: Andrew Schweinfurth, Chicago, IL (US); Julija Alegra Petkus, Oak Park, IL (US)

(73) Assignee: WALGREEN CO., Deerfield, IL (US)

( * ) Notice: Subject to any disclaimer, the term of this patent is extended or adjusted under 35 U.S.C. 154(b) by 0 days.

(21) Appl. No.: 16/427,624

(22) Filed: May 31, 2019

(51) Int. Cl.
  *G06T 19/00* (2011.01)
  *G06F 3/01* (2006.01)
  *G16H 20/10* (2018.01)
  *G06F 9/451* (2018.01)

(52) U.S. Cl.
  CPC ............ *G06T 19/006* (2013.01); *G06F 3/011* (2013.01); *G06F 9/451* (2018.02); *G16H 20/10* (2018.01)

(58) Field of Classification Search
  CPC combination set(s) only.
  See application file for complete search history.

(56) References Cited

U.S. PATENT DOCUMENTS

| | | | | |
|---|---|---|---|---|
| 10,552,575 | B1* | 2/2020 | Mohebbi | G06K 9/4609 |
| 2007/0185736 | A1* | 8/2007 | Cervi | G16H 20/10 |
| | | | | 705/2 |
| 2011/0257989 | A1* | 10/2011 | Kumar | G16H 20/10 |
| | | | | 705/2 |
| 2013/0260360 | A1* | 10/2013 | Baurmann | G06F 3/013 |
| | | | | 434/365 |
| 2015/0161341 | A1* | 6/2015 | Van De Craen | G06K 9/18 |
| | | | | 705/2 |
| 2015/0242592 | A1* | 8/2015 | Weiss | G16H 10/60 |
| | | | | 705/2 |
| 2016/0259996 | A1* | 9/2016 | Hartley | G06K 9/00671 |
| 2016/0314276 | A1* | 10/2016 | Wilz, Sr. | G06F 19/3462 |
| 2018/0032680 | A1* | 2/2018 | Chen | G16H 20/10 |
| 2018/0190375 | A1* | 7/2018 | Chapela | A61B 5/486 |
| 2018/0336411 | A1* | 11/2018 | Schuh | H04N 5/232 |
| 2019/0336682 | A1* | 11/2019 | Colleran | G16H 20/10 |
| 2019/0392934 | A1* | 12/2019 | Tabakin | G16H 10/60 |
| 2020/0312437 | A1* | 10/2020 | Wendland | G16H 20/17 |

* cited by examiner

*Primary Examiner* — Andrew G Yang
(74) *Attorney, Agent, or Firm* — Marshall, Gerstein & Borun LLP

(57) ABSTRACT

Methods and systems may provide an augmented reality (AR) pharmaceutical interface to a client electronic device such as a mobile smartphone. The AR pharmaceutical interface may identify one or more prescription products (e.g., consumable products or medical devices) appearing in a field of view of a camera of the electronic device. Based upon the identified prescription product(s), the AR pharmaceutical interface may provide augmentations such as visual overlays, audial feedback, and/or other information associated with the identified prescription product(s). In some implementations, the AR pharmaceutical interface may facilitate other prescription-related functions, such as refills and/or transfers, by launching a dedicated prescription application at the electronic device.

15 Claims, 10 Drawing Sheets

AUGMENTED REALITY PHARMACEUTICAL INTERFACE

FIELD OF THE DISCLOSURE

The present disclosure generally relates to augmented reality systems, and, more particularly, to an augmented reality (AR) interface that may provide prescription-related information and to facilitate other prescription-related functions.

BACKGROUND

Recent advancements in digital image recognition and distributed computing techniques have allowed for implementation of digital image recognition at portable electronic devices such as smartphones, tablets, and the like. In particular, mobile applications have emerged that allow for substantially real-time recognition of digital images captured via a built-in camera of a portable electronic device. As an example, Google Lens™, provided by Google LLC, enables image recognition of text and other image content captured via a dedicated camera application or another application at the portable electronic device.

In view of these advancements, there exists an opportunity to improve existing technological practices of computer-implemented ordering, refilling, and usage of pharmaceutical drugs and other products. Existing desktop and mobile applications, such as those provided by Walgreen Company, enable consumers to electronically manage prescriptions and order prescription products. However, careful attention is required of the consumer both to correctly identify prescription products for ordering, and to consume those products according to proper dosing standards.

SUMMARY

The present disclosure relates generally to systems and methods that may provide an augmented reality (AR) pharmaceutical interface to an electronic device, such as a mobile smartphone. The AR system may utilize image recognition techniques to identify one or more prescription products in a frame of view of a camera ("camera frame"), and may provide visual augmentations and/or other AR content to the electronic device for display via an AR interface, to thereby provide prescription-related information and facilitate other prescription-related functions to a user of the electronic device. The information and functions provided to the user via the AR interface may include, for example, dosing information relating to a prescription product, refill information relating to the prescription product, and/or various other functions for ordering, refilling, and/or transferring a prescription for the product.

In one embodiment, a computer-implemented method is provided. The method may include (1) receiving, via one or more processors, image data from a real-world environment corresponding to a field of view of a camera associated with an electronic device, (2) identifying, via the one or more processors, based upon an analysis of the image data, one or more prescription products appearing in the field of view of the camera, (3) obtaining, via the one or more processors, information corresponding to the one or more identified prescription products, (4) generating, via the one or more processors, content to be provided at the electronic device via an augmented reality interface, the content indicative of at least a portion of the obtained information corresponding to the one or more identified prescription products, and/or (5) causing, via the one or more processors, the generated content to be displayed via the augmented reality interface of the electronic device. The method may include additional, fewer, and/or alternate actions, including actions described herein.

In another embodiment, another computer-implemented method is provided. The method may include (1) capturing, via one or more camera devices communicatively associated with an electronic device, image data corresponding to a real-world environment, (2) transmitting, via one or more processors, the image data to one or more servers, (3) receiving, via the one or more processors, augmented reality content for display via an augmented reality interface of the electronic device, and/or (4) displaying, via the augmented reality interface, the received augmented reality content at a display of the electronic device. The method may include additional, fewer, and/or alternate actions, including actions described herein.

In still another embodiment, a computing system is provided. The system may include one or more processors, and one or more computer memories storing non-transitory computer-executable instructions that, when executed via the one or more processors, cause the computing system to (1) receive image data from a real-world environment corresponding to a field of view of a camera associated with an electronic device, (2) identify, based upon an analysis of the image data, one or more prescription products appearing in the field of view of the camera, (3) obtain information corresponding to the one or more identified prescription products, (4) generate content to be provided at the electronic device via an augmented reality interface, the content indicative of at least a portion of the obtained information corresponding to the one or more identified prescription products, and/or (5) cause the generated content to be displayed via the augmented reality interface of the electronic device. The system may include additional, fewer, or alternate components, and/or may perform additional, fewer, or alternate actions, as described herein.

BRIEF DESCRIPTION OF THE DRAWINGS

The figures described below depict various embodiments of the system and methods disclosed herein. It should be understood that each figure depicts an embodiment of a particular embodiment of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

There are shown in the drawings arrangements which are presently discussed, it being understood, however, that the present embodiments are not limited to the precise arrangements and instrumentalities shown, wherein.

Figure 1:
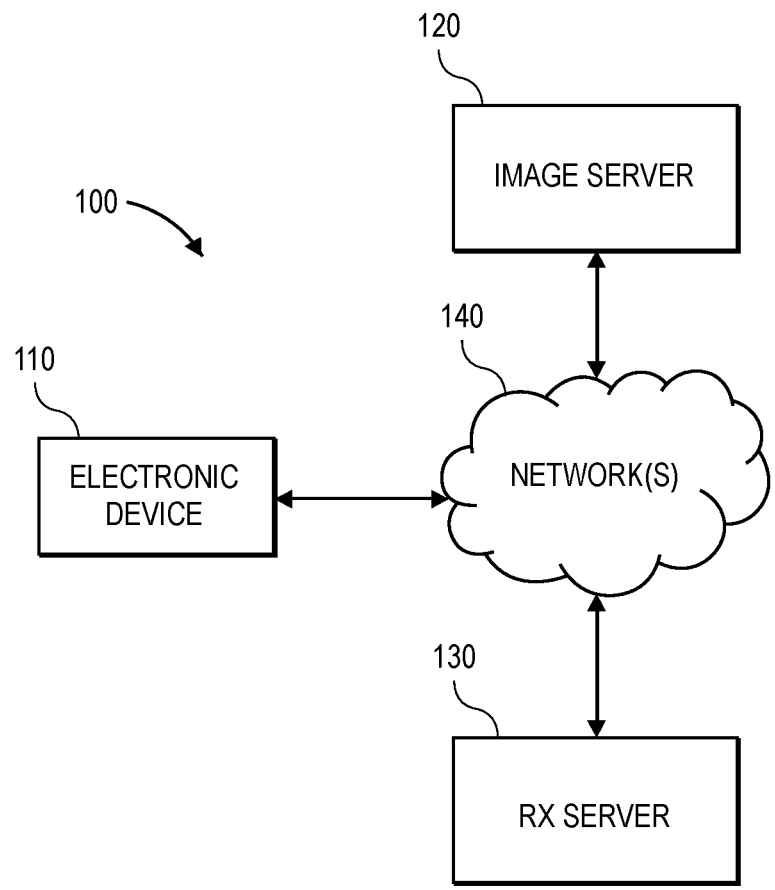
FIG. 1 depicts an example environment including components and entities associated with an AR pharmaceutical interface, in accordance with some embodiments.

The Figures depict embodiments for purposes of illustration only. One skilled in the art will readily recognize from the following discussion that alternative embodiments of the systems and methods illustrated herein may be employed without departing from the principles of the invention described herein.

DETAILED DESCRIPTION

The present embodiments relate to, inter alia, systems and methods that may provide an augmented reality (AR) pharmaceutical interface to an electronic device to thereby enable a user of the electronic device to (1) access information corresponding to prescription products (e.g., dosing/usage instructions, disposal instructions, ingredients, etc.), (2) refill an order for a prescription product, and/or (3) transfer an existing prescription to a particular prescription product provider.

In an aspect, a user of an electronic device (e.g., a smartphone) may utilize one or more AR applications to access a camera device (or simply "camera," e.g., an internal and/or external device for recording image and/or video). The one or more AR applications may include, for example, a native AR-enabled camera application of the mobile electronic device, and/or another third-party, AR-enabled image/video capturing application (e.g., Google Lens™, a visual search engine compatible with various mobile electronic devices and offered by Google LLC). In some embodiments, one or more AR applications may be implemented at least in part via one or more servers, and via communications between the one or more electronic device and the one or more servers via one or more networks. In any case, the user may utilize the one or more applications to capture one or more prescription products within a field of view of the camera device ("camera frame"). The prescription product may be, for example, a pill bottle or another container holding a consumable prescription product, or some other product prescribed for consumption or other use.

As described herein, "capturing [an object] within the camera frame," and similar language, refers to causing the camera device to be aimed and/or focused open the object such that the object is within a current field of view of the camera device, such that the object may be visible via a display screen corresponding to the current camera frame. As will be understood from the present disclosure, capturing the object within the camera frame may not require that the user actively capture a still image and/or video containing the object. That is, the AR system according to aspects described herein may provide the AR functions described herein, for example, while a camera device is in a "preview" mode or otherwise operating in a mode without capturing still images or recording video content. Accordingly, "image data," as described herein, may refer to data corresponding to a camera frame regardless of whether a still image or recorded video was actively taken by the user.

The AR system may, in accordance with aspects described herein, receive and analyze image data corresponding to the camera device. In some embodiments, the electronic device of the user may automatically transmit real-time image data via one or more networks to one or more servers, which may analyze received image data to (1) identify one or more prescription products in the image data and (2) provide various AR augmentations to a display and/or other I/O device of the electronic device. In some embodiments, one or more processors of the electronic device itself may implement at least a portion of the image recognition and/or other techniques described herein. In any case, one or more prescription products may be identified from the image data, for example, based upon a machine-readable code (e.g., PDF417, Code 39 barcode, QR code, or other code) present in the image data corresponding to prescription product, text identifying the prescription product (e.g., via optical character recognition), and/or other based upon various other image recognition techniques.

Upon identification of the one or more prescription products in the image data, information associated with the one or more prescription products may automatically be obtained, for example, via one or more prescription servers via the one or more networks, via one or more image servers via the one or more networks, and/or via one or more other applications stored and/or executed at the electronic device (e.g., a mobile prescription application). Information associated with the one or more prescription products may include, for example, dosing/usage information, disposal instructions, ingredient or manufacturer information, side effects, and/or other information described herein.

In some embodiments, information associated with the one or more prescription products may relate more particularly to a prescription previously provided to the user and corresponding to the one or more identified prescription products. In such scenarios, it is preferable, and often required by law, that such sensitive information be protected from access by authorized individuals. Accordingly, in some embodiments, the AR system may, for example, facilitate protected access for a user to patient-specific prescription information by providing a link or other redirect to a website, application, and/or other service via which the user may appropriately authenticate and access such sensitive information.

Upon identification of one or more prescription products captured in the camera frame, the AR system may be configured to provide one or more AR augmentations within the context of the AR application(s) to indicate the identified prescription product(s), and/or provide other information or functions corresponding to the prescription products. AR augmentations may include, for example, various visual, auditory, and/or haptic augmentations. A visual AR augmentation may, for example, include a visual overlay (e.g., a container box or dot) provided over or around the prescription product itself within the display corresponding to the camera device, and may include information associated with the prescription product. Additionally or alternatively, a visual overlay may include a tab or expandable bar providing prescription-related information and/or controls to facilitate the prescription-related functions described herein.

As the user of the electronic device continues to use the one or more AR application(s), the AR system may automatically modify the visual AR augmentations and/or other AR augmentations in real time, in accordance with the current camera frame and the objects depicted therein. That is, the AR system may add, remove, and/or modify the position and/or content of visual AR augmentations and/or other AR augmentations based upon moving, zooming, and/or other distortions of the camera frame. Moreover, such modification of the AR interface may be provided in response to user interactions with the AR augmentation(s) or other aspects of the AR interface.

"Augmented reality" (AR), as described herein, generally refers to an experience of a real-world environment that is artificially modified via computer-generated perceptual information, and which may be implemented via various AR computing systems, including various combinations of hardware and/or software described herein. Perceptual information ("AR augmentations") provided via an AR system may include, but is not limited to, visual, auditory, and/or haptic information, which may be at least partially interactive, and which may be constructive and/or destructive in nature. An "augmented reality interface" or "AR interface," as used herein, may refer more particularly to user-facing aspects (e.g., "front-end" components) of the AR system via which a user may access information and functions as described herein, which may be enabled via other aspects of the AR system (e.g., "back-end" components). Via the techniques described herein, the AR interface may provide AR augmentations substantially in real time, based upon real-time identification of objects captured in the field of view of a camera device associated with a user device. As described herein, "real time" refers to the execution of computing actions without unnecessary delays for data indexing, storage, etc., although some lag time for data transmission and/or processing may be necessary.

As used herein, a "prescription" may refer to an instruction (e.g., a written instruction) provided via a physician and authorizing a patient (e.g., a patient using the AR system described herein) to be provided one or more prescription products ("prescribed product(s)," e.g., a consumable medication, a topical medication, or a medical device). In some instances, a "prescription" may refer simply to a prescription product itself. A "refill" for a prescription, as used herein, may refer to (1) an instruction/authorization for the patient to be provided at least a partial replacement of one or more prescription products, and/or (2) the act of execution of such an instruction/authorization. Accordingly, information pertaining to prescriptions, as described herein, may include, for example, (1) use, dosing, and/or disposal instructions for a prescription product, (2) information regarding ingredients (e.g., active ingredients) and/or manufacturers of a prescription product, (3) product warnings or side effects relating to a prescription product, (4) general refill or reorder instructions for a prescription product, and/or (5) details of an active or past prescription corresponding to a particular patient (e.g., patient-specific dosing/use/refill instructions, a time and/or location associated with retrieving a prescription product, etc.). Accordingly, AR functions relating to prescriptions, as described herein, may include (1) accessing patient-specific information relating to a prescription, (2) accessing general information relating to a prescription product, (3) refilling a prescription, and/or (4) transferring a prescription to a particular retail pharmacy or provider.

It should be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based upon any statement made in any section of this patent (other than the language of the claims). To the extent that any term recited in the claims at the end of this disclosure is referred to in this disclosure in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based upon the application of 35 U.S.C. § 112, sixth paragraph.

I. Example Environment

FIG. 1 illustrates an example environment 100 associated with providing an augmented reality (AR) pharmaceutical interface to an electronic device 110. Although FIG. 1 depicts certain entities, components, and devices, it should be appreciated that additional or alternate entities and components are envisioned.

As depicted in FIG. 1, the environment 100 may include an electronic device 110 (i.e., one or more electronic devices). The electronic device 110 may be, for example, a smart phone, a desktop computer, a laptop, a tablet, a phablet, a smart watch, smart glasses, wearable electronics, pager, personal digital assistant, and/or any other electronic device, particularly including computing devices configured for wireless radio frequency (RF) communication. The electronic device 110 may store and/or one or more AR applications, prescription applications, and/or other applications via which the electronic device 110 may utilize the AR system described herein. The electronic device 110 may include one or more camera devices (e.g., an optical camera) for capturing the external physical environment ("real-world environment") around the electronic device 110. Such one or more camera devices may include a camera physically integrated into the electronic device 110, an external camera communicatively connected to the electronic device 110, or some combination thereof. As used herein, a "camera-enabled" electronic device 110 may refer to an electronic device having one or more native camera devices within, and/or being communicatively connected to one or more external camera devices, so as to be able to capture an external physical environment based upon which an AR pharmaceutical interface may be provided.

The electronic device 110 may store machine-readable code representative of one or more AR applications stored on a memory therein. To access the capabilities of the AR system described herein, a user of the electronic device may, for example, launch the one or more AR applications to access an AR interface, which may enable the electronic device 110 to capture one or more prescription products and display various AR augmentations described herein, to thereby access prescription product information and/or access various other functions described herein.

The electronic device 110 may communicate with an image server 120 and/or with a prescription server ("Rx server") 130 via a network 140 (i.e., one or more networks). The network 140 may facilitate any type of data communication via any standard or technology (e.g., GSM, CDMA, TDMA, WCDMA, LTE, EDGE, OFDM, GPRS, EV-DO, UWB, IEEE 802 including Ethernet, WiMAX, WiFi, Bluetooth, and/or others). The network 140 may be a public network, such as the Internet, or a private network such as an LAN or intranet. In some embodiments, the electronic device 110 may, at predetermined intervals, transmit data representative of digital images to the image server 120.

The image server 120 may, substantially in real time, identify one or more objects (e.g., prescription products) present in the image data received at the image server 120. To identify one or more prescription products, the image server 120 may utilize various feature detection techniques, edge detection techniques, and/or other techniques (e.g., scale-invariant feature transform (SIFT), speeded up robust features (SURF), fast retina keypoint (FREAK), binary robust invariant scalable keypoints (BRISK), etc.). The image server 120 may, in particular, employ feature detection techniques based upon template images and/or other objects known to correspond to or include prescription products (e.g., an image known to depict a prescription product). Via these and/or other image recognition techniques, the image server 120 may receive image data and continuously track the location (e.g., position within the camera frame) of one or more prescription products included in the image data.

In response to identifying one or more prescription products in the received image data, the image server 120 may generate and/or provide various AR content to the electronic device 110 via the network 140. The image server 120 may, for example, generate audio data, color values, orientation, scale, and/or positions within the camera frame for AR augmentations, and may generate and/or transmit signals to the electronic device 110 to cause the electronic device 110 to locally generate and/or provide the AR augmentations.

In some embodiments, the image server 120 may communicate with the Rx server 130 via the network 140. For example, in some embodiments, the image server 120 may, in response to identifying one or more prescription products based upon image data, query the Rx server 130 to receive information associated with the one or more prescription products, at least some of which the image server 120 may provide to the electronic device 110 via one or more AR augmentations. Additionally or alternatively, in some embodiments, the image server 120 may communicate with the Rx server to receive information regarding prescription transfers, refills, and/or other functions that may be available for a prescription device, such that the AR interface at the electronic device 110 may facilitate performance of such prescription functions via the AR interface.

The AR interface provided via the electronic device 110 may enable a user of the electronic device 110 to receive information associated with one or more prescription products. In some embodiments, one or more AR augmentations provided via the interface may be interactive. The user may, for example, provide input such as a touch screen interaction, button press, or voice command to interact with the AR interface. User interaction at the electronic device 110 may cause further communications among the electronic device 110, image server 120, and/or Rx server 130, for example, to identify further information regarding prescription products, and/or to carry out other prescription-related functions (e.g., launching and/or logging into a prescription application at the electronic device 110, transferring an existing prescription, refilling a prescription, etc.).

Various modifications to the environment 100 are possible. In some embodiments, for example, the image server 120 and Rx server 130 may be combined into one set of one or more servers. The environment 100 may include additional, fewer, and/or alternate computing components.

Figure 2:
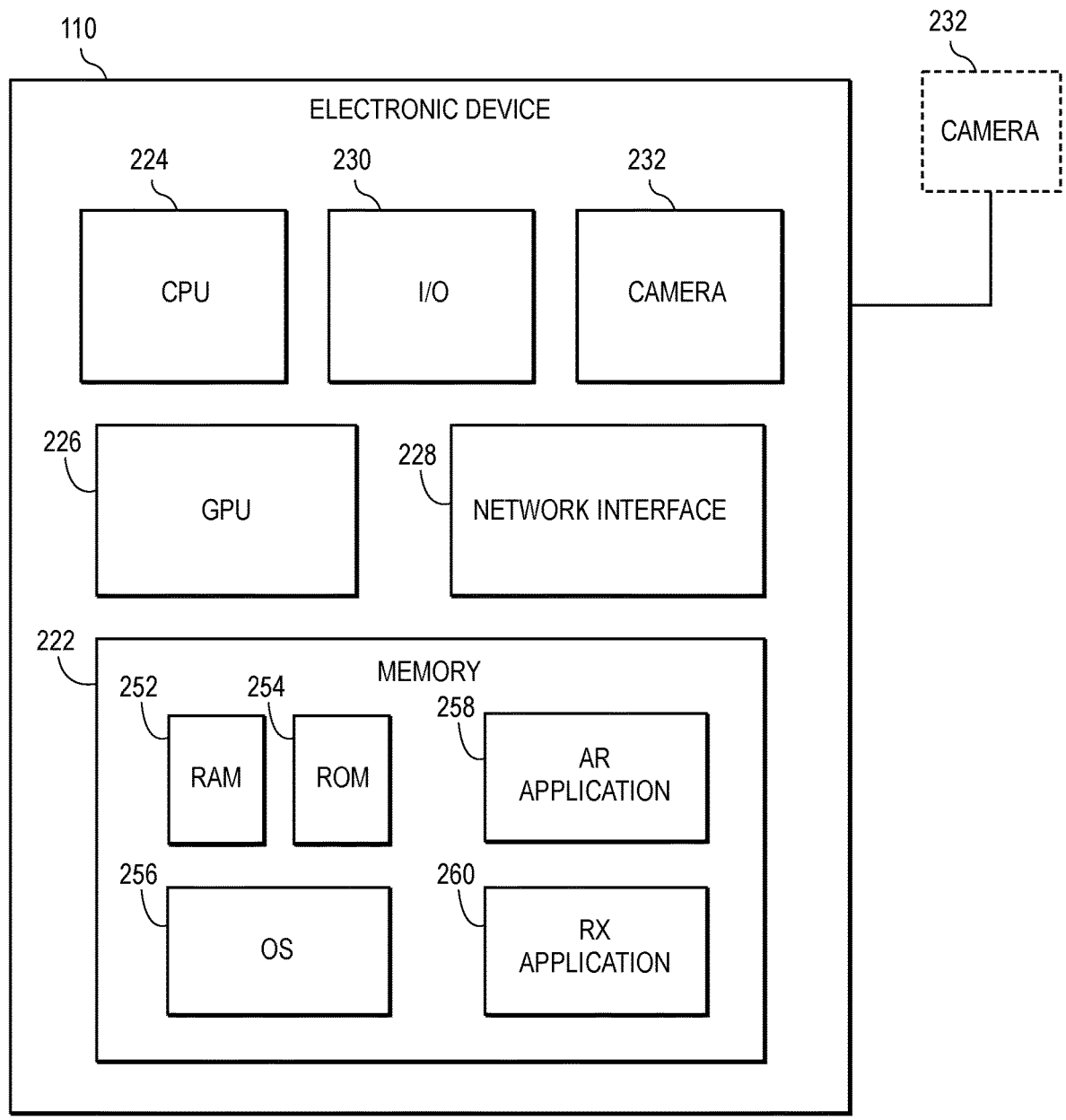
FIG. 2 depicts an example electronic device via which an AR pharmaceutical interface may be provided, in accordance with some embodiments.

FIG. 2 provides further illustration of an example electronic device 110 that may implement the techniques described herein, in some embodiments. The electronic device 110 may be, for example, a smartphone, tablet device, desktop computer, laptop computer, wearable device (e.g., smart watch or headset) and/or other suitable electronic device. The electronic device 110 may include a memory 222, a processor (CPU) 224, and a graphics processing unit (GPU) 226. The electronic device 110 may further include a network interface 228, which may facilitate communications to and/or from the electronic device 110 over one or more networks (e.g., network 140 as depicted in FIG. 1). Still additionally or alternatively, the electronic device 110 may include an I/O 230 and/or camera 232. In some embodiments, the camera 232 may be an internal camera native to the electronic device 110. Additionally or alternatively, the camera 232 may be an external camera communicatively connected to the electronic device 110 via the I/O 230, via the network interface 228, and/or via other suitable means.

The memory 222 (i.e., one or more memories) may include a non-transitory, computer readable memory comprising computer-executable instructions that, when executed, cause the electronic device to perform actions thereof described in this description (e.g., via the CPU 224, GPU 226, and/or other components of the electronic device 110 or greater system 100). The memory 222 may comprise suitable memory modules such a random access memory (RAM) 252, read-only memory (ROM) 254, flash memory, and/or other types of persistent memory. The memory 222 may store an operating system (OS) 256, which may implement applications such as an augmented reality (AR) application 258 and/or a prescription (Rx) application 260. In some embodiments, the OS 256 may include API functions that allow two or more applications or modules (e.g., two or more applications at the electronic device 110) to interface with each other. The OS 256 may, for example, facilitate linking of prescription-related functions provided via the Rx application 260 to an AR interface provided via the AR application 258.

The I/O 230 (i.e., one or more input and/or output units) may include, for example, or more visual displays, one or more touch devices (e.g., touchpad or touchscreen), a keyboard, a mouse, one or more speakers, one or more microphones, one or more vibration devices, and/or other suitable input and/or output devices. In some embodiments, the I/O 230 may include one or more peripheral I/O devices, such as a peripheral display screen or microphone communicatively connected to the electronic device 110 (e.g., via a wired or wireless connection).

In particular, the I/O 230 may include a display screen that display a camera frame corresponding to the camera 232, and upon which various visual AR augmentations may be provided. Such AR augmentations may be provided, for example, via the AR application 256 interfacing with the camera 232 and/or the I/O 230.

In an example implementation of some of the AR interface techniques described herein, a user of the electronic device 110 may access the AR application 258, which may be configured to provide an AR interface by interfacing with the camera 232 and causing a corresponding display of the camera frame to be provided at the electronic device 110 (e.g., via a native display screen and/or peripheral display). The AR application may cause image data corresponding to the camera frame to be transmitted from the electronic device 110 (e.g., via the network interface 228) over one or more networks (e.g., the network 140) to one or more servers (e.g., the image server 120). The one or more servers may analyze the image data and identify one or more prescription products depicted therein. In some embodiments, the one or more servers may locate and/or retrieve additional information associated with the one or more prescription products (e.g., via the Rx server 130). The one or more servers may generate one or more AR augmentations for the electronic device 110 (e.g., parameters of one or more visual, audial, and/or haptic AR augmentations).

The one or more servers may transmit, via the one or more networks, information to the electronic device 110 indicative of the generated AR augmentations, such that the electronic device 110 may provide the AR augmentations via the AR interface. Such AR augmentations may comprise various information associated with a prescription product (e.g., dosing or usage information, and/or other information described herein). Additionally or alternatively, such AR augmentations may facilitate various functions associated with a prescription product. For example, an AR augmentation may comprise a button linking to a prescription provider application (e.g., Rx application 260), such that the user may transfer a prescription, refill a prescription, or perform other prescription-related tasks described herein (upon the user providing credentials as appropriate within the application).

The electronic device 110 may continue to transmit and/or receive data from the one or more servers, such that the AR interface may be updated substantially in real time to reflect one or more prescription products currently captured in the camera frame, and/or to reflect various user interactions with the AR interface and AR augmentations provided therein.

The electronic device 110 may include additional, fewer, and/or alternate components, and may be configured to perform additional, fewer, or alternate actions, including components/actions described herein.

II. Example Augmented Reality Actions

Figure 3:
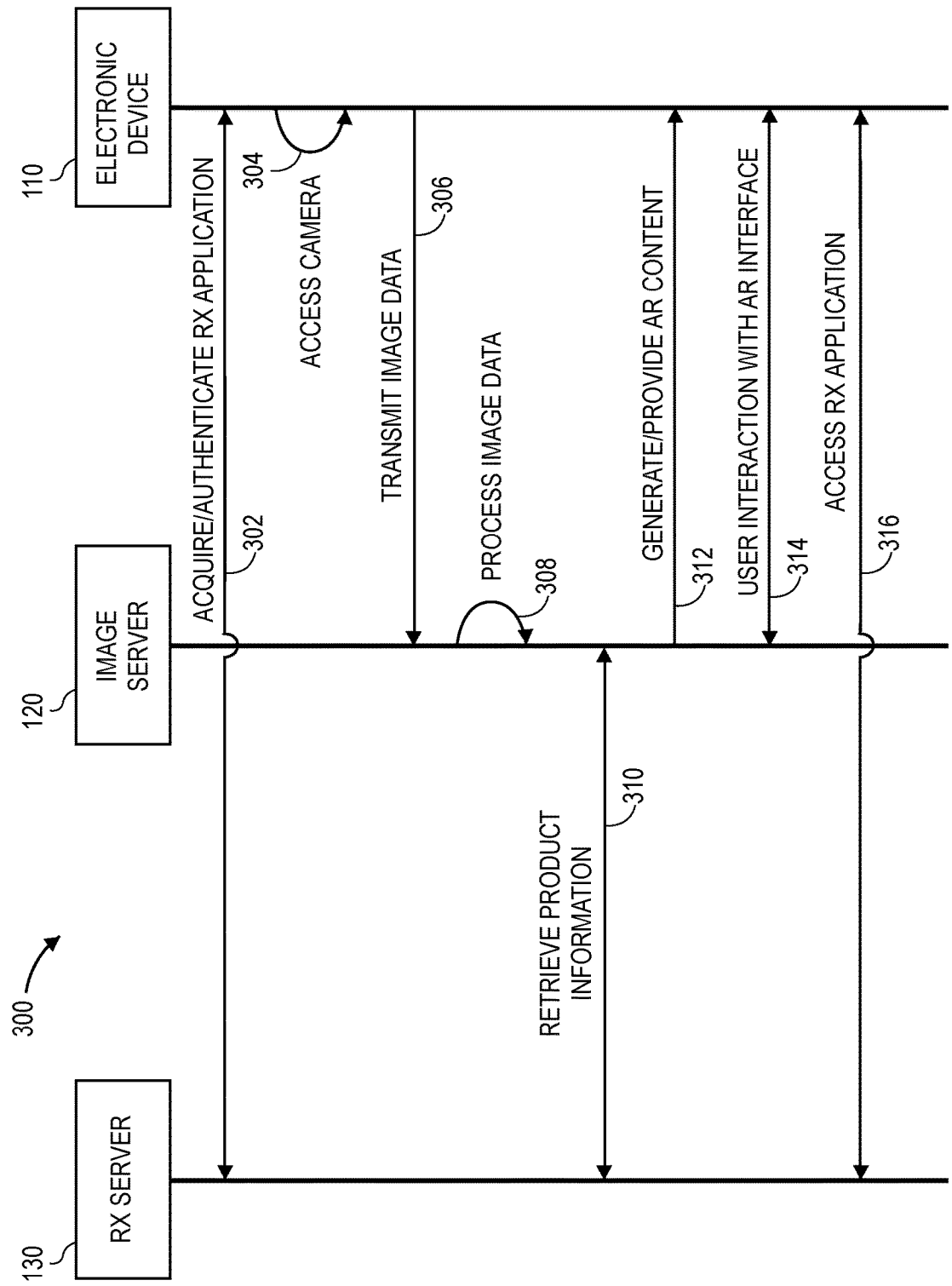
FIG. 3 is a signal diagram depicting computing actions that may be performed to provide an AR pharmaceutical interface.

Referring to FIG. 3, illustrated is a signal diagram 300 associated with providing an augmented reality (AR) pharmaceutical interface. Actions depicted in the signal diagram may be performed via computing devices depicted in FIGS. 1 and 2, in some embodiments. For example, as depicted in FIG. 3, the AR pharmaceutical interface may be provided via interactions among an electronic device 110 (e.g., the device and user thereof), an image server 120, and/or an Rx server 130, any of which may communicate via one or more networks. Additional, fewer, and/or alternate actions may be included. In various embodiments, an order of actions depicted in the signal diagram 300 may vary.

An electronic device may optionally acquire and/or authenticate one or more prescription (Rx) applications (302). An Rx application may, for example, be an application provided by one or more pharmaceutical providers to allow users to order, refill, transfer, etc., various prescription products which are prescribed to the user by a physician. The prescription application may be acquired, for example, via one or more application distribution services (e.g., Google Play™ store). Once acquired, the Rx application may require user authentication, which may include (1) creating a user account for secure login to the Rx application, (2) logging into the created user account (e.g., upon each attempt to access the Rx application), and/or (3) registering active prescriptions, nearby pharmacies, and/or other user-specific information. Acquisition Rx application may allow elements of the AR pharmaceutical interface to direct a user to the Rx application upon identification of one or more prescription products in a camera frame. Importantly, authentication via the Rx application may enable a user to access sensitive, user-specific information via the Rx application upon proper authentication (and not, for example, within the camera frame as displayed via the AR application).

The electronic device 110 may access a camera device (e.g., internal or external camera), for example, via a dedicated AR application and/or other camera-enabled application (304). A user of the electronic device 110 may point, zoom, and/or otherwise manipulate the camera to capture one or more prescription products in the frame thereof. In particular, the user may point the camera so as to capture a text element, barcode, QR code, or other information that may identify a prescription product (e.g., to identify a product labeled upon a pill bottle). For some prescription products, simply capturing the product itself in the camera frame may be sufficient (e.g., a medical device identifiable by shape, size, color, etc.).

The electronic device 110 may transmit image data corresponding to the camera frame to the image server 120 (306). Such communication may occur substantially in real time. That is, as the user of the electronic device 110 manipulates the camera so as to modify the camera frame (e.g., zoom, reposition, refocus, etc.), the electronic device 110 may continue to transmit current image data to the image server 120.

The image server 120 may receive image data transmitted via the electronic device 110, and may analyze the received image data to determine that one or more prescription products are depicted therein (308). The image server may utilize various feature detection techniques, edge detection techniques, and/or other techniques (e.g., scale-invariant feature transform (SIFT), speeded up robust features (SURF), fast retina keypoint (FREAK), binary robust invariant scalable keypoints (BRISK), etc.). The image server 120 may, in particular, employ feature detection techniques based upon template images and/or other objects known to correspond to or include prescription products (e.g., an image known to depict a prescription product). The image server 120 may determine that a prescription product is depicted in the image data via recognition of a machine-readable code (e.g., barcode or QR code) a text element, and/or other information identifying the prescription product.

The image server 120 may communicate with the Rx server 130 to retrieve information associated with one or more prescription products (310). For example, where a text element or machine-readable code is identified in the image data, the image server 120 may query the Rx server 130 to identify a prescription product corresponding to the text element or machine-readable code. Additionally or alternatively, upon identification of a particular prescription product, the image server 120 may query the Rx server 130 to obtain information associated with the particular prescription product (e.g., product dosing or usage instructions, product side effects or warnings, and/or other prescription-related information described herein).

In some implementations, the image server 120 may query the Rx server 130 to obtain information indicating what prescription-related functions may be available to a patient associated with a particular prescription product. Some products, such as consumable prescription products, may generally be capable of being refilled. Other products, such as some medical devices, are not typically refilled, but rather may be routinely inspected for defect, and/or reordered if defective. A prescription for a particular product may, for example, be transferrable between two different pharmacies or providers.

The image server 120 may generate and/or provide AR content to the electronic device 110 (312). The AR content may include various visual, audial, haptic, and/or other perceptual information (AR augmentations) to be provided via an AR interface of the electronic device 110. Generating a visual augmentation may, for example, include determining a position, size, color, text content, image content, and/or other visual characteristic of an element to be provided within the camera frame of the electronic device 110. As another example, generating an audial augmentation may include determining a sound and volume thereof to be output at the electronic device 110. Providing AR content may include transmitting data to the electronic device 110, the data corresponding to one or more AR augmentations and causing the electronic device to provide the one or more AR augmentations via the AR interface (e.g., substantially in real time). Examples of AR augmentations are provided with respect to FIGS. 4A-4F.

Various user interactions with the AR interface at the electronic device 110 may occur (314). A user may, for example, use a touch screen or other input to interact with a particular visual AR augmentation within the camera frame. As another example, the user may provide a voice command corresponding to one of the AR augmentations. In some embodiments, responsive to user interaction with an AR augmentation, the electronic device may communicate with the image server 120 to obtain further AR augmentations so as to provide an interactive AR experience at the electronic device 110.

The signal diagram 300 may include accessing the Rx application via the Rx server 130 (316). In some embodiments, for example, interaction with an AR augmentation may cause the electronic device to launch the Rx application or a particular feature therein (e.g., to transfer an existing prescription, to refill a prescription, to contact a physician, or to access other patient-specific information). In some embodiments, even when a particular product or prescription is identified from image data based upon interactions between the image server 120 and the Rx server 130, viewing any patient-specific information associated with the product or prescription may take place only within the Rx application. In any case, accessing the Rx application may require login or other authentication to ensure security of privileged patient information.

III. Example Augmented Reality (AR) Interface

FIGS. 4A-4F depict example displays of an augmented reality (AR) pharmaceutical interface in accordance with aspects of the techniques described herein. These example displays may be displayed at an electronic device, such as the electronic device 110 depicted in FIGS. 1-3 (e.g., a smartphone, tablet, laptop computer, and/or other camera-enabled device described herein). The example displays may be provided, for example, via computing interactions between the electronic device and one or more servers communicating via one or more networks (e.g., the servers 120 and 130 and the network 140, as depicted in FIGS. 1-3).

Figure 4A:
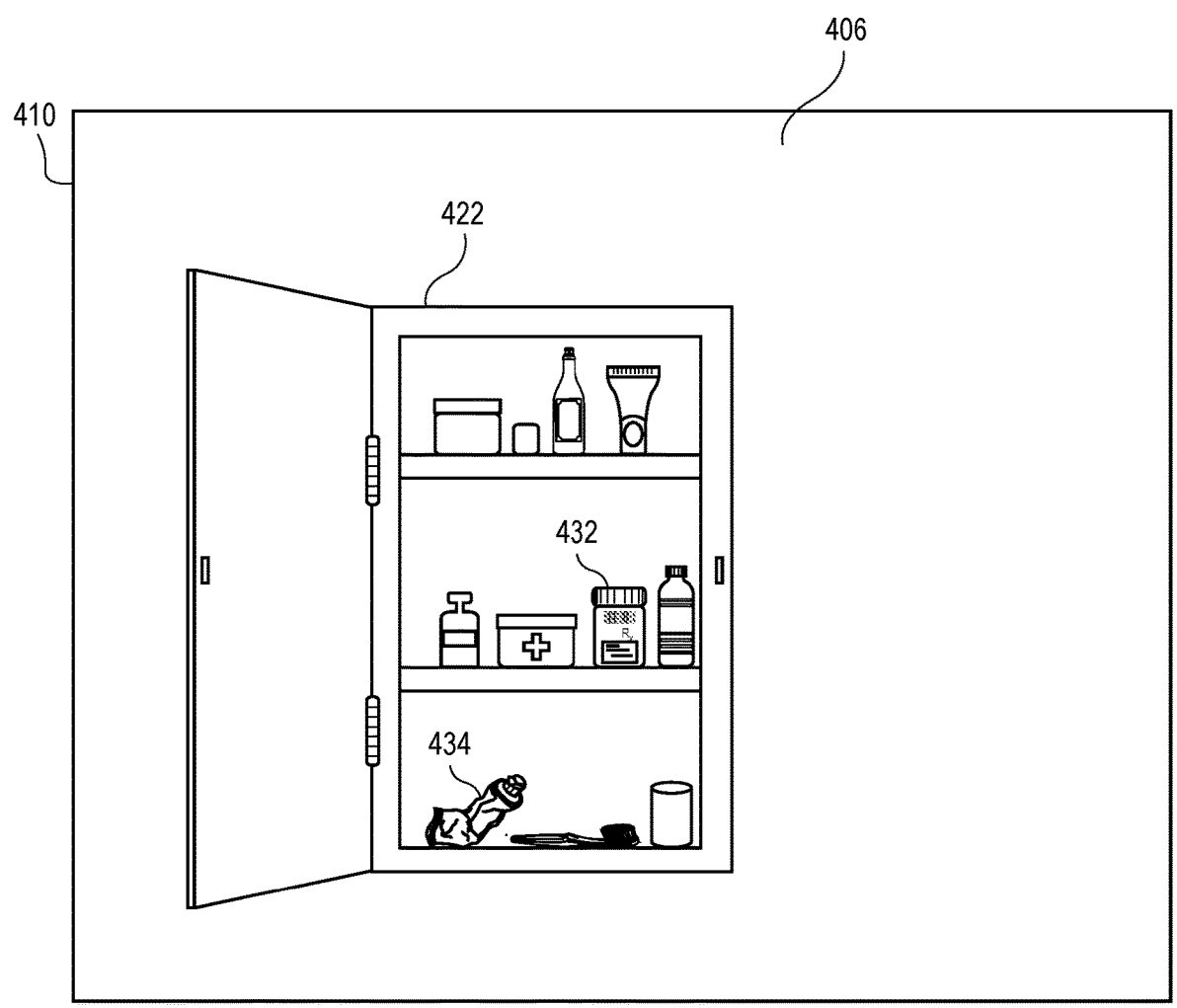
FIGS. 4A-4F depict example displays of an AR pharmaceutical interface, in accordance with some embodiments.

Referring first to FIG. 4A, the AR interface depicts a portion of a real-world environment 406 within a bounding box 410, which may be associated with the boundary of a camera frame. More particularly, the bounding box 410 may correspond to the boundary of a display (e.g., touchscreen display) of the electronic device, or at least a portion thereof, upon which the camera frame is visually depicted to enable various camera and AR functions. For example, with reference to FIGS. 1-3, the bounding box 410 may correspond to the boundary of a display of the electronic device 110 (e.g., internal and/or external display(s), I/O 230), which display visually represents the contents of a camera frame of the camera device 232 (i.e., external and/or internal camera). For purposes of this description, phrases such as "[an object] is displayed" or "[an object] appears in the frame," or similar language, may refer to the object being within the bounding box 410 so as to be displayed at the display of the electronic device.

Still referring to FIG. 4A, the real-world environment 406 includes a medicine cabinet 422. The medicine cabinet 422 includes three shelves, which may hold a number of personal hygiene items, grooming items, cosmetic items, over-the-counter (i.e., non-prescription) medical products, and/or other items. Of particular interest among items in the medicine cabinet 422 are (1) prescription medication bottle 432 (in this example, containing a number of doses of lisinopril, a prescription medication commonly used to treat high blood pressure and other conditions), and (2) a prescription inhaler 434, which may commonly be prescribed to treat asthma and/or to deliver a controlled quantity of a prescription medication to the lungs of a patient. While the medication bottle 432 and inhaler 434 are depicted herein, various other prescription products may be envisioned, including but not limited to consumable medications, topical prescription products, and/or medical devices.

Figure 4B:
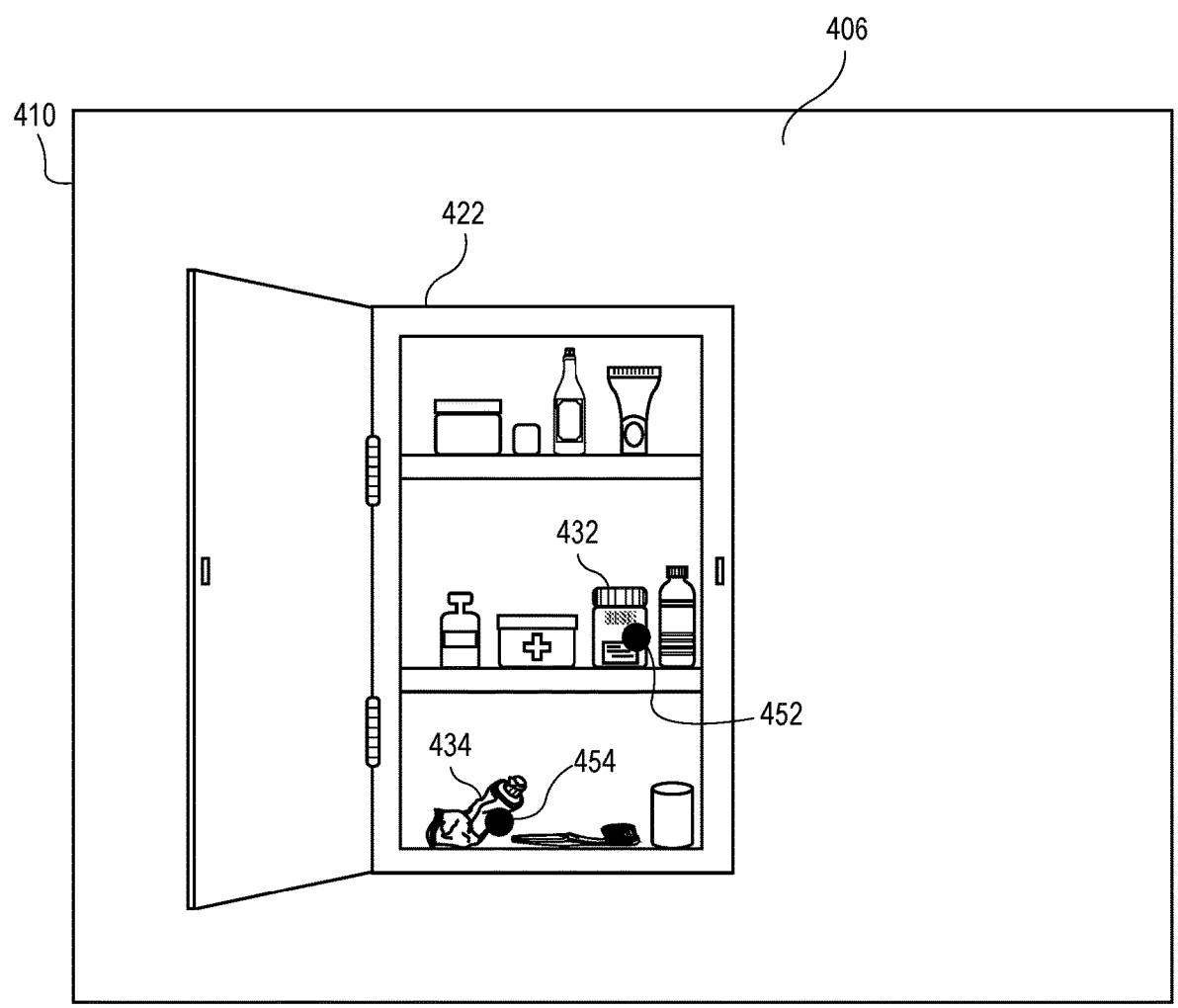

FIG. 4B depicts the AR interface including a similar view of the real-world environment 406 as in FIG. 4A, but modified via two visual AR augmentations 452 and 454, which may be provided based upon a determination that one or more prescription products appear in the camera frame (e.g., within the portion of the real-world environment 406 within the bounding box 410). Specifically, the first augmentation 452 is a 'dot' indicating the presence of the medication bottle 432, and the second augmentation 454 is a second dot indicating the presence of the prescription inhaler 454. Various other visual, audial, haptic, and/or other AR augmentations may be provided to indicate the presence of a prescription product, in other embodiments. The presence of the prescription product may be detected, for example, based upon identification of a text string, barcode, image, object shape/size, and/or other digital image analysis techniques, including techniques described herein.

Figure 4C:
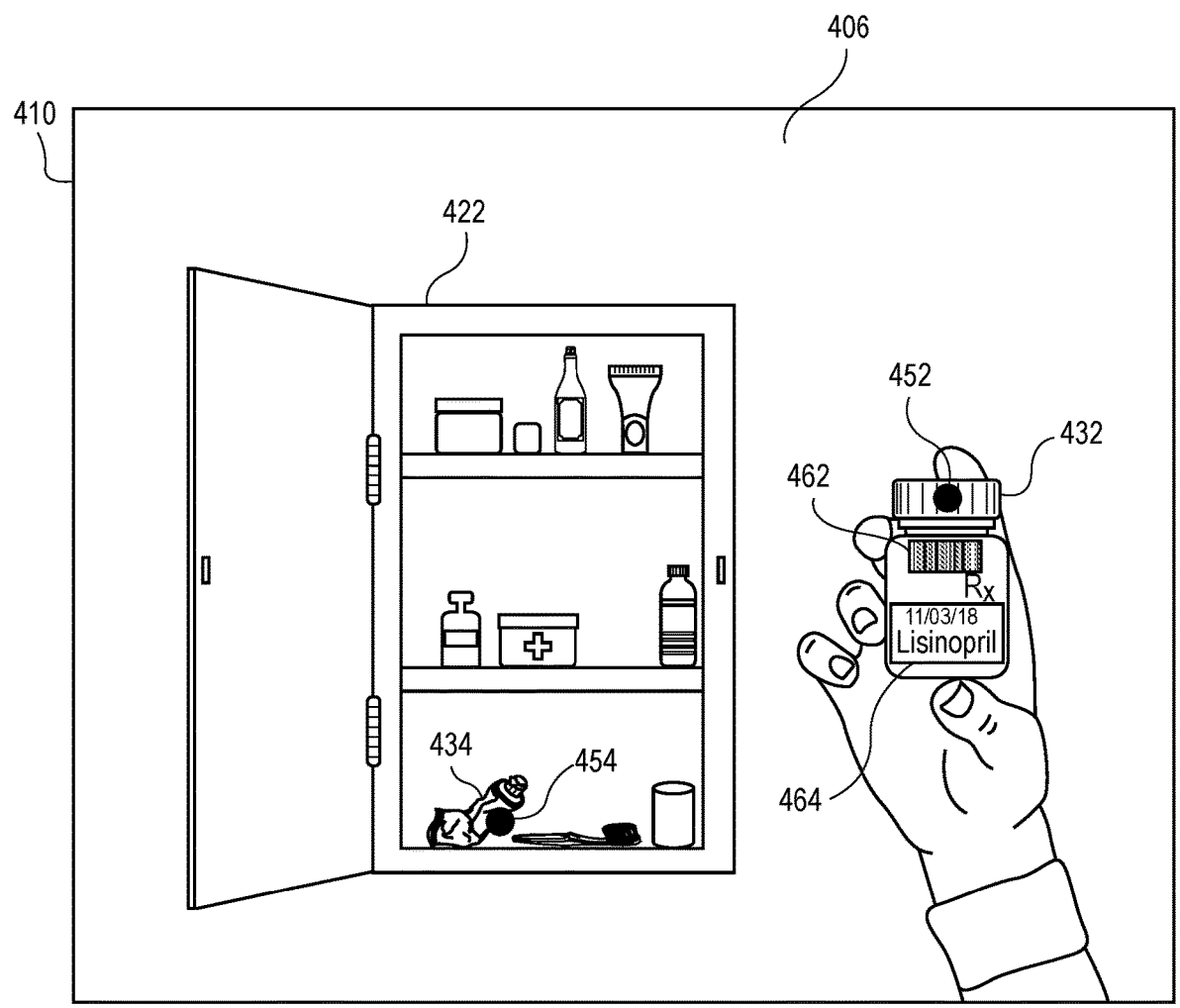

FIG. 4C depicts the AR interface of FIGS. 4A and 4B, with the prescription medication bottle 432 removed from a shelf of the medicine cabinet 422 by a human patient (e.g., shortly prior to consuming the prescription medication). As shown in FIG. 4C, the AR augmentation 452 moves within the AR interface to follow the current location of the medication bottle 432. Because the AR interface may provide image analysis substantially in real-time, visual AR augmentations and/or other AR augmentations may be provided to identify and track prescription products in accordance with changes in the camera frame (e.g., scanning, zooming, refocusing, and/or other operations that change the scope of the camera frame). Additionally or alternatively to the augmentation 452, AR augmentations may include boxes 462 and 464 to indicate the particular image elements based upon which the prescription product was identified (e.g., a barcode, prescription date, and/or product name depicted on a label of the product).

Figure 4D:
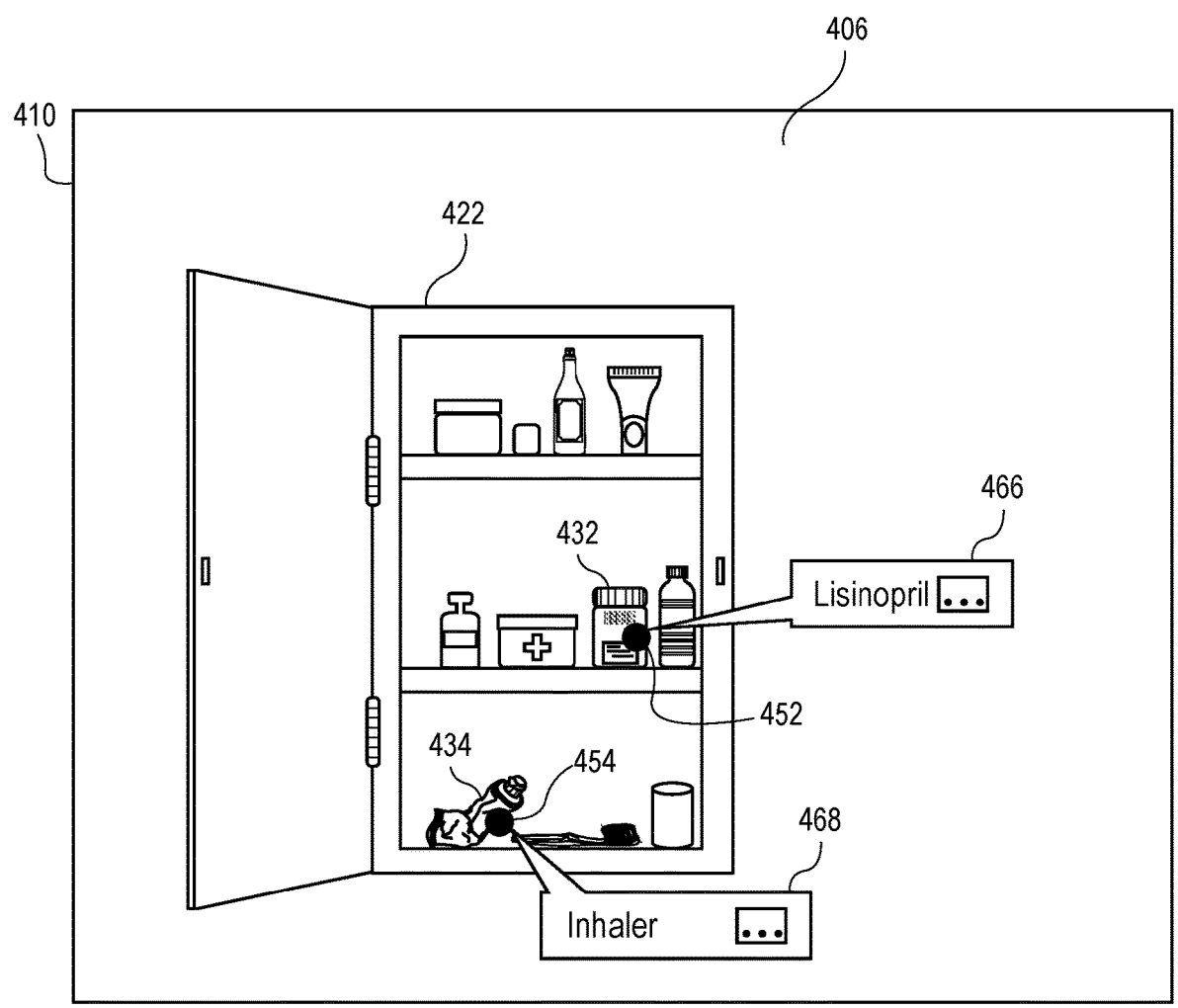

FIG. 4D depicts the AR interface of FIGS. 4A-4C, with further visual AR augmentations 466 and 468 provided based upon identification of the prescription products appearing in the camera frame. Specifically, an overlay 466 identifies the medication bottle 432, and the overlay 468 identifies the inhaler 434. In some implementations, the AR interface may provide the augmentations 466 and/or 468 in response with a user interaction with the augmentations 452 and/or 454, respectively. That is, in response to a user interaction with a first AR augmentation (e.g., a touchscreen tap, swipe, voice command, key press, etc.), the AR interface may provide one or more further AR augmentations to provide additionally information corresponding to the same prescription product as the first AR augmentation.

Figure 4E:
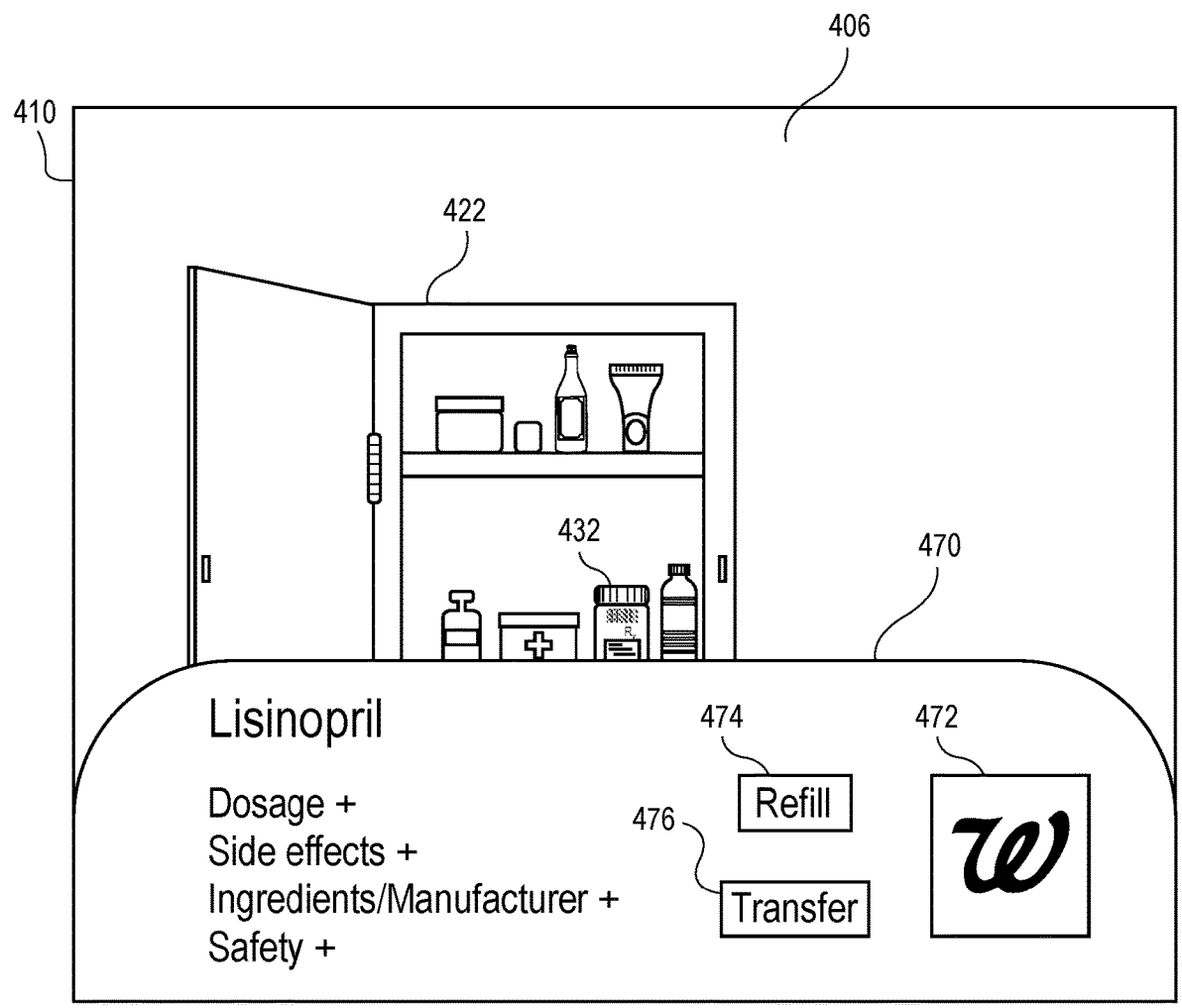

FIG. 4E depicts the AR interface of FIGS. 4A-4D, with further visual AR augmentations that may be provided, for example, based upon identification of a prescription product in the camera frame, and/or based upon user interaction with one or more previously provided AR augmentations. Particularly, a tab 740 occupies approximately a lower third of the display, obscuring a portion of the camera frame. The tab 470 may be "locked" in position, such that it remains visible upon the display screen regardless of changes in the camera frame (e.g., changing views of the environment 406 due to scan, zoom, refocusing, and/or other operations of the camera).

Within the tab 470, various other information and controls are provided. An icon 472 may, for example, link to a means for downloading a prescription application (e.g., Google Play™ store) or, if the prescription application has already been downloaded, may invoke an API to launch a home screen and/or other functions of the prescription application. Similarly, a refill control 474 and/or a transfer control 476 may, upon selection (e.g., touch or voice command), invoke an API to launch corresponding features of the prescription application.

In some embodiments, the AR interface may interface with the prescription application and/or the prescription server to determine what functions are available for a particular prescription product. For example, in some implementations, the refill control 474 may be provided only upon a determination that (1) the identified prescription product was provided by a provider of the prescription application (e.g., by a Walgreens pharmacy, as identified based upon a barcode or other machine-readable code on the prescription product), and/or (2) the prescription product is capable of being refilled (e.g., as is the case for a consumable medication, but not some medical devices). Similarly, in some implementations, the transfer control 476 may be provided only upon a determination that (1) the application provider offers the identified prescription product, and (2) the identified prescription product has a barcode or other machine-readable code that is readable but not identifiable, thus indicating that the prescription product was not originally provided by the application provider (but can be transferred). Additional or alternative controls may be provided, in other embodiments. For example, in some implementations, one or more AR augmentations may invoke an API for replacing a defective medical device, providing patient-specific dosing/usage instructions, contacting a physician or pharmacist, and/or performing other prescription-related functions.

Still referring to FIG. 4E, the tab 470 includes further information associated with the identified prescription product. In this case, the tab 470 includes an overview of general recommended dosage information, side effects, chemical ingredients and manufacturing information, and safety information (e.g., disposal recommendations and/or overdose warnings). For each information header, a control 478 may be included, such that a user interaction with the control 478 (e.g., tap, swipe, or voice command) may cause further AR augmentations to be provided (e.g., visual and/or audial augmentations providing further information).

Figure 4F:
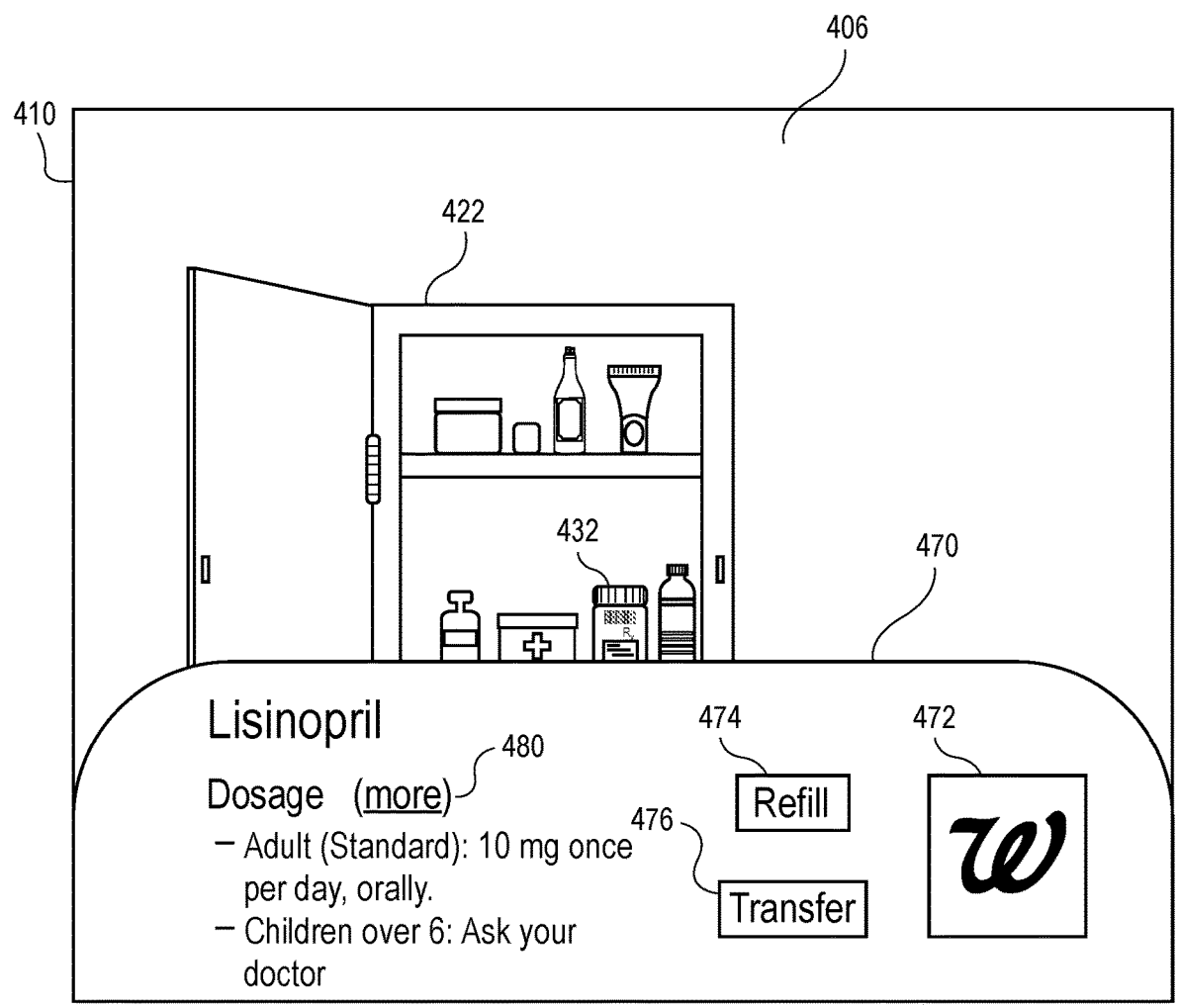

FIG. 4F depicts the AR interface of FIGS. 4A-4E, with the "dosage" header expanded, for example, in response to user interaction with the control 478. In this case, general dosage information provides recommendations for adults and/or children consuming the identified prescription product. Due to security considerations, patient-specific dosage information and other patient-specific information may be restricted from appearing in the AR interface, but may in some implementations be provided via a prescription application linked by the AR interface (e.g., via controls 472, 474, and/or 476). A user interaction with a "more" control 480 may cause the AR interface to launch a web browser, a dedicated prescription application, and/or another application which may provide further information and/or functions corresponding to a prescription product as appropriate.

Referring to FIGS. 4E and 4F, the tab 470 and its contents (and/or any other AR augmentations) may be dismissed via a user interaction, such as a voice command, a button press (e.g., a "back" button or other button navigation at an electronic device), and/or a downward swipe of the tab 470 toward the bottom of the display screen. Thus, a user of the AR interface may manipulate the AR augmentations provided therein to view additional information or less information, or to return to a natural view of the camera frame.

While FIGS. 4A-4F depict example displays of an AR pharmaceutical interface, it should be appreciated that various other implementations are possible. The AR interface may operate to provide various visual, audial, haptic, and/or other AR augmentations, including any appropriate combinations thereof.

IV. Example Server and/or Client Methods

Figure 5:
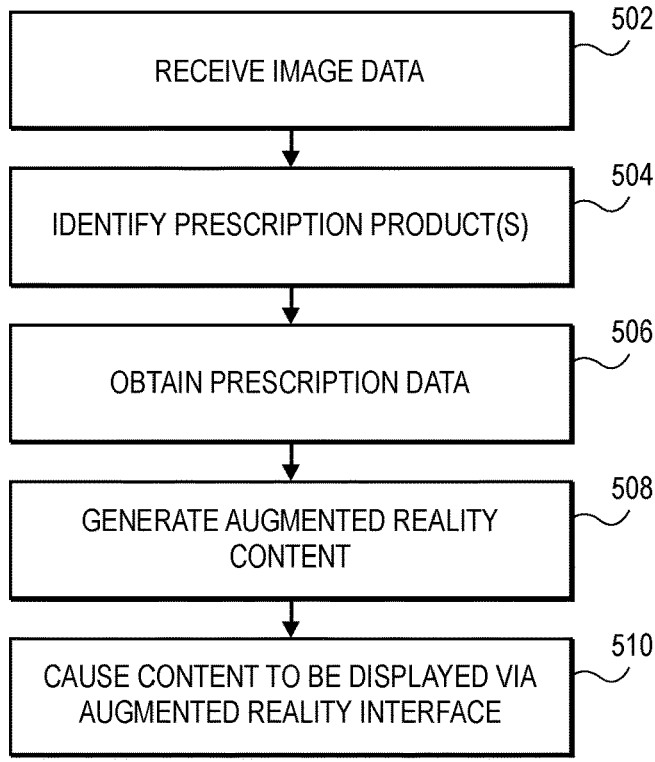
FIGS. 5 and 6 depict example computer-implemented methods for providing an AR pharmaceutical interface, in accordance with some embodiments.

FIG. 5 depicts an example computer-implemented method 500 for providing an augmented reality (AR) pharmaceutical interface. Generally, the method 500 may be performed via computing components depicted in FIGS. 1-3, and/or by other suitable computing components. More particularly, actions of the method 500 may be performed by one or more servers (e.g., server(s) 120 and/or 130). Actions of the method 500 may be performed, for example, to produce an AR interface as depicted and described with reference to one or more of FIGS. 4A-4F. In some embodiments, one or more computer memories (and/or other non-transitory computer-readable media) may store computer executable instructions that, when executed via one or more processors, cause one or more computing devices to perform actions of the method 500.

The method 500 may include receiving image data, e.g., example image data captured via one or more cameras of an electronic device and relating to a real-world environment (502). Such one or more cameras include one or more internal cameras and/or one or more external cameras associated with the electronic device.

The method 500 may include, subsequent to receiving the image data, identify one or more prescription products included in the image data (504). As used herein, one or more prescription products "included in the image data" or "depicted in the image data" may refer to the one or more prescription products being in a portion of the real-world environment captured in a frame of a camera such that the presence of the one or more prescription products is detectable from the image data. Generally, "identifying" a prescription product may comprise a determining whether or not a prescription product is included in the image data, and may more particularly include specifically identifying the product itself.

The one or more prescription products may be detected and/or identified by way of various image analysis techniques, such as SIFT, SURF, FREAK, BRISK, and/or other image analysis techniques such as those described herein. In particular, in some embodiments, one or more prescription products may be detected and/or identified via detection of a machine-readable code included in the image data (e.g., barcode). In some circumstances, a prescription product may be identified based upon the machine-readable code by referencing the machine-readable code to a prescription database (e.g., at Rx server 130). However, in other circumstances, for example, wherein the machine-readable code was produced by another pharmacy, physician, etc., and thus data may not be available that identifies the prescription product from the machine-readable code. It should be appreciated, though, that the prescription product may still be identified based upon other image analysis techniques described herein.

The method 500 may include obtaining data corresponding to one or more identified prescription products (506). Information corresponding to any one prescription product may include, for example, dosing and/or usage instructions, safety warnings, disposal instructions, side effects, physician/pharmacy contact information, manufacturer information, active ingredient(s), and/or other information described herein. Such information may be obtained, for example, via one or more prescription servers (e.g., Rx server 130).

The method 508 may include generating augmented reality content for display at the electronic device (508). Augmented reality content may include various AR augmentations, such as visual, audial, and/or haptic AR augmentations described herein. Visual AR augmentations may include, for example, various AR augmentations as depicted in FIGS. 4A-4F. Generating augmented reality content may include generating computer-executable instructions that, when transmitted to the electronic device, cause the electronic device to provide one or more AR augmentations.

The method 500 may include causing the generated content to be displayed via the augmented reality interface of the electronic device 510). Causing the generated content to be displayed may include transmitting computer-executable instructions and/or one or more AR augmentations, to thereby cause the one or more AR augmentations to be displayed at the electronic device (e.g., cause a visual overlay to be provided, a sound or vibration to be executed, etc.).

The method 500 may further include receiving user interaction data, which may, for example, be indicative of user interaction with an AR augmentation via the user interface (e.g., via a touch, swipe, button press, etc.). In some embodiments, the method 500 may include generating further AR content to be displayed via the electronic device based upon the user interaction data, and/or causing the further AR content to be displayed via the electronic device.

The AR pharmaceutical interface described herein may provide an AR experience at the electronic device substantially in real-time, such that the AR interface at the electronic device updates in accordance with a display of the camera frame. Accordingly, in some embodiments, any or all actions of the method 500 may be performed repeatedly or continuously, based upon the camera frame and/or based upon received user interaction data.

In some embodiments, the method 500 may include obtaining and/or transmitting further information associated with one or more identified products, for example, to facilitate performance of a prescription transfer, prescription refill, or other prescription-related function at an electronic device of a user (e.g., via a dedicated prescription application of the electronic device).

The method 500 may include additional, fewer, and/or alternate actions, in some embodiments. Moreover, in some embodiments, the order of actions of the method 500 may differ from the order described above.

Figure 6:
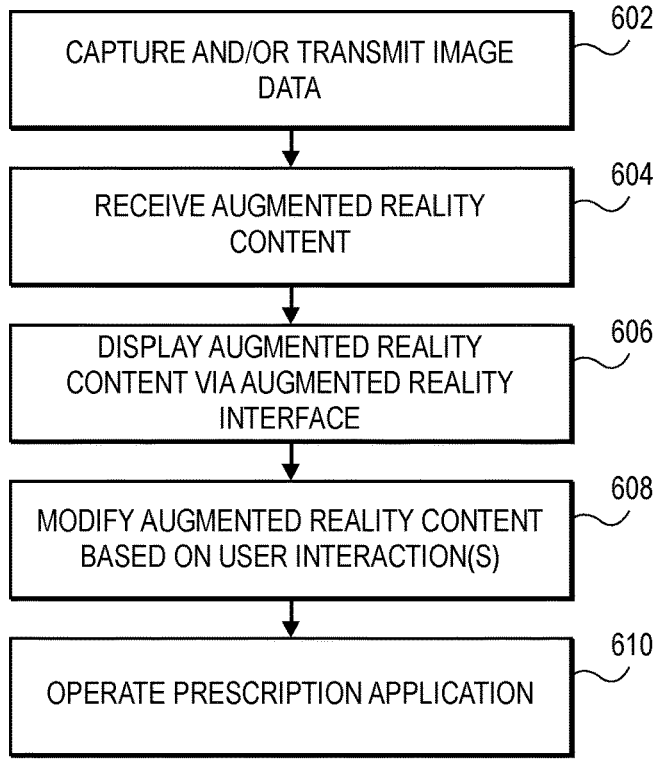

FIG. 6 depicts another example computer-implemented method 600 for providing an augmented reality (AR) pharmaceutical interface. Generally, the method 600 may be performed via computing components depicted in FIGS. 1-3, and/or by other suitable computing components. More particularly, actions of the method 600 may be performed by one or more electronic devices (e.g., device 110, also referred to as "client device"). Actions of the method 600 may be performed, for example, to produce an AR interface as depicted and described with reference to one or more of FIGS. 4A-4F. In some embodiments, one or more computer memories (and/or other non-transitory computer-readable media) may store computer executable instructions that, when executed via one or more processors, cause one or more computing devices to perform actions of the method 600.

The method 600 may include capturing and/or transmitting image data corresponding to a real-world environment (602) via an electronic device. The image data may be captured, for example, via one or more AR and/or camera applications, in conjunction with one or more internal and/or external camera devices of the electronic device. The image data may be transmitted, for example, via one or more transceivers to one or more servers for detection/identification of one or more prescription products.

The method 600 may further include receiving AR content for display via an AR interface of the electronic device (604). The AR content may be received, for example, via one or more image servers and/or one or more prescription servers (e.g., servers 120 and/or 130). The received AR content may, for example, indicate AR augmentations to be provided with respect to elements of the image data detected/identified to be one or more prescription products. Accordingly, the received AR content may comprise various data associated with the one or more prescription products.

The method 600 may further include displaying AR content (e.g., one or more AR augmentations) via one or more displays of the electronic device, which one or more displays may correspond to a frame of the camera device (606). The one or more displays may include various display/output devices described herein, such as internal and/or external visual displays, speakers, vibration devices, etc. The AR content may be displayed via an AR interface of the electronic device, e.g., as provided via one or more AR applications stored at the electronic device. Displaying AR content may include causing one or more user controls to be displayed via the AR interface (e.g., controls for interacting with the camera device, interacting with an AR augmentation, and/or launching a prescription application to perform one or more prescription-related functions).

The method 600 may include modifying the displayed AR content based upon user interaction with the AR interface (608). That is, the method 600 may include (1) detecting an input of the user at the electronic device (e.g., a touch, swipe, button press, voice command, and/or other input corresponding to the AR interface or a particular AR augmentation therein), (2) transmitting data indicative of the user interaction to one or more servers, and/or (3) receiving and/or displaying further AR content generated and provided according to the user interaction data.

The method 600 may further include operating a prescription application at the electronic device (610). Operating the prescription application may, for example, include causing the prescription application to launch via invocation of an API in response to user interaction via the AR interface. The prescription application may operate, for example, to facilitate a prescription refill, transfer, re-order, and/or other prescription related function.

The AR pharmaceutical interface described herein may provide an AR experience at the electronic device substantially in real-time, such that the AR interface at the electronic device updates in accordance with a display of the camera frame. Accordingly, in some embodiments, any or all actions of the method 600 may be performed repeatedly or continuously, based upon the camera frame and/or based upon received user interaction data.

The method 600 may include additional, fewer, and/or alternate actions, in some embodiments. Moreover, in some embodiments, the order of actions of the method 600 may differ from the order described above.

V. Additional Considerations

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

What is claimed:

1. A computer-implemented method comprising:
   receiving, via one or more processors, image data from a real-world environment corresponding to a field of view of a camera associated with a mobile electronic device;
   identifying, via the one or more processors, based upon an analysis of the image data, a plurality of prescription products appearing in the field of view of the camera;
   obtaining, via the one or more processors, information corresponding to each of the plurality of identified prescription products;

generating, via the one or more processors, content to be provided at the mobile electronic device via an augmented reality interface, the content indicative of at least a portion of the obtained information corresponding to each of the plurality of identified prescription products;

causing, via the one or more processors, at least a portion of the generated content to be displayed via the augmented reality interface of the mobile electronic device, the displaying of the at least the portion of the generated content comprising displaying, for each of the plurality of identified prescription products, an interactive user interface element selectable to display further information corresponding to the respective prescription product; and responsive to a selection of the interactive user interface element corresponding to a selected prescription product from among the plurality of identified prescription products, causing, via the one or more processors, display at the mobile electronic device of (i) the further information corresponding to the selected prescription product, and (ii) an additional one or more interactive user interface elements selectable to automatically access a dedicated prescription application at the mobile electronic device to access protected patient information associated with the selected prescription product.

2. The method of claim 1, wherein the information corresponding to a particular product from among the plurality of identified prescription products comprises information indicating one or more of: dosing guidelines for the particular product; one or more side effects of the particular product; one or chemical ingredients of the particular product; a manufacturer of the particular product; and safety information associated with the particular product.

3. The method of claim 1, wherein causing the generated content to be displayed comprises causing one or more visual overlays to be superimposed over a display of the field of view of the camera at the mobile electronic device.

4. The method of claim 1, wherein the causing of the generated content to be displayed via the augmented reality interface comprises causing the content to be displayed substantially in real-time, such that the content is displayed via the augmented reality interface while at least one of the plurality of identified prescription products remains in the field of view of the camera.

5. The method of claim 1, wherein identifying a particular product from among the plurality of identified prescription products includes:

detecting, via the one or more processors, based upon the image data, a unique machine-readable code corresponding to the particular product.

6. The method of claim 5, further comprising:
determining, via the one or more processors, based upon the detected machine-readable code, a provider of a prescription associated with the particular product;

and wherein the displaying of the additional one or more interactive user interface elements comprises, upon selection of the interactive user interface element for the particular product, displaying, based upon the determination of the provider, one or more controls selectable to initiate at least one of a prescription refill or a prescription transfer for the particular product via the dedicated prescription application at the mobile electronic device.

7. A computer-implemented method, comprising:
capturing, via one or more camera devices communicatively associated with a mobile electronic device, image data corresponding to a real-world environment;

transmitting, via one or more processors, the image data to one or more servers;

receiving, via the one or more processors, augmented reality content for display via an augmented reality interface of the mobile electronic device;

displaying, via the augmented reality interface, the received augmented reality content at a display of the electronic device, the displayed augmented reality content comprising, for each of a plurality of prescription products identified from the image data, an interactive user interface element selectable to display further information corresponding to the respective prescription product; and upon a selection of the interactive user interface element corresponding to a selected prescription product from among the plurality of identified prescription products, displaying, at the mobile electronic device, (i) the further information corresponding to the selected prescription product, and (ii) an additional one or more interactive user interface elements selectable to automatically access a dedicated prescription application at the mobile electronic device to access protected patient information associated with the selected prescription product.

8. The computer-implemented method of claim 7, wherein the image data comprises a unique machine-readable code identifying a particular one of the plurality of prescription products.

9. The computer-implemented method of claim 8, wherein the displaying of the additional one or more interactive user interface elements comprises, upon selection of the interactive user interface element for the particular one of the plurality of prescription products, displaying one or more controls selectable to initiate at least one of a prescription refill or a prescription transfer for the particular one of the plurality of prescription products via the dedicated prescription application at the mobile electronic device.

10. A computing system comprising:
one or more processors; and
one or more computer memories storing non-transitory computer-executable instructions that, when executed via the one or more processors, cause the computing system to:

receive image data from a real-world environment corresponding to a field of view of a camera associated with a mobile electronic device;

identify, based upon an analysis of the image data, a plurality of prescription products appearing in the field of view of the camera;

obtain information corresponding to each of the plurality of identified prescription products;

generate content to be provided at the mobile electronic device via an augmented reality interface, the content indicative of at least a portion of the obtained information corresponding to each of the plurality of identified prescription products;

cause at least a portion of the generated content to be displayed via the augmented reality interface of the mobile electronic device, the displaying of the at least the portion of the generated content comprising displaying, for each of the plurality of identified prescription products, an interactive user interface element selectable to display further information corresponding to the respective prescription product; and responsive to a selection of the interactive user interface element corresponding to a selected prescription product from among the plurality of identified prescription products, cause display at the mobile electronic device of (i) the further information corresponding to the selected prescription product, and (ii) an additional one or more interactive user interface elements selectable to automatically access a dedicated prescription application at the mobile electronic device to access protected patient information associated with the selected prescription product.

11. The computing system of claim 10, wherein the information corresponding to a particular product from among the plurality of identified prescription products comprises information indicating one or more of: dosing guidelines for the particular product; one or more side effects of the particular product; one or chemical ingredients of the particular product; a manufacturer of the particular product; and safety information associated with the particular product.

12. The computing system of claim 10, wherein causing the generated content to be displayed comprises causing one or more visual overlays to be superimposed over a display of the field of view of the camera at the mobile electronic device.

13. The computing system of claim 10, wherein the causing of the generated content to be displayed via the augmented reality interface comprises causing the content to be displayed substantially in real-time, such that the content is displayed via the augmented reality interface while at least one of the plurality of identified prescription products remains in the field of view of the camera.

14. The computing system of claim 10, wherein identifying a particular product from among the plurality of identified prescription products includes:

detecting, based upon the image data, a unique machine-readable code corresponding to the particular product.

15. The computing system of claim 14, wherein the computer-executable instructions, when executed via the one or more processors, further cause the computing system to:

determine, via the one or more processors, based upon the detected machine-readable code, a provider of a prescription associated with the particular product;

and wherein the displaying of the additional one or more interactive user interface elements comprises, upon selection of the interactive user interface element for the particular product, displaying, based upon the determination of the provider, one or more controls selectable to initiate at least one of a prescription refill or a prescription transfer for the particular product via the dedicated prescription application at the mobile electronic device.

* * * * *